(12) United States Patent
Jeon et al.

(10) Patent No.: US 9,044,146 B2
(45) Date of Patent: Jun. 2, 2015

(54) ARM-FASTENING DEVICE FOR PULSE DIAGNOSIS, PULSE SENSOR, PULSE DIAGNOSIS APPARATUS COMPRISING THE DEVICE AND SENSOR, AND METHOD FOR MANUFACTURING PULSE SENSOR

(75) Inventors: Young Ju Jeon, Daejeon (KR); Young Jae Woo, Daejeon (KR); Hyun Hee Ryu, Kyeonggi-do (KR); Jong Yeol Kim, Daejon (KR)

(73) Assignee: Korea Institute of Oriental Medicine (KR)

( * ) Notice: Subject to any disclaimer, the term of this patent is extended or adjusted under 35 U.S.C. 154(b) by 885 days.

(21) Appl. No.: 13/122,656

(22) PCT Filed: Jun. 9, 2009

(86) PCT No.: PCT/KR2009/003077
§ 371 (c)(1),
(2), (4) Date: Jun. 22, 2011

(87) PCT Pub. No.: WO2010/041807
PCT Pub. Date: Apr. 15, 2010

(65) Prior Publication Data
US 2011/0257543 A1    Oct. 20, 2011

(30) Foreign Application Priority Data

Oct. 6, 2008  (KR) .......................... 10-2008-0097830
Mar. 10, 2009  (KR) .......................... 10-2009-0020277

(51) Int. Cl.
*A61B 5/02*    (2006.01)
*A61B 5/021*   (2006.01)
*A61B 5/022*   (2006.01)
*A61B 5/00*    (2006.01)

(52) U.S. Cl.
CPC . *A61B 5/021* (2013.01); *A61B 5/02* (2013.01); *A61B 5/022* (2013.01); *A61B 5/6831* (2013.01); *A61B 5/702* (2013.01)

(58) Field of Classification Search
CPC ............ A61B 5/02; A61B 5/021; A61B 5/022
USPC ........................................ 600/481, 500–503
See application file for complete search history.

(56) References Cited

U.S. PATENT DOCUMENTS 7,554,167 B2 *  6/2009  Vaganov ...................... 257/415
8,632,471 B2 *  1/2014  Lee et al. ..................... 600/500
(Continued)

FOREIGN PATENT DOCUMENTS

KR    1020020096224 A    12/2002
KR    1020030069743 A     8/2003
(Continued)

OTHER PUBLICATIONS

"PCT International Search Report dated Jan. 18, 2010 for PCT/KR2009/003077, from which the instant application is based," 2 pgs.

*Primary Examiner* — Jacqueline Cheng
*Assistant Examiner* — Puya Agahi
(74) *Attorney, Agent, or Firm* — Fredrikson & Byron P.A.

(57) ABSTRACT

The present invention relates to an arm-fastening device for a pulse diagnosis, a pulse sensor, a pulse diagnosis apparatus comprising the device and sensor, and a method for manufacturing the pulse sensor. Embodiments of the present invention permit the pulse of a person to be examined to be correctly measured in the state in which the person to be examined is a comfortable one when the pulse of the person to be examined is being measured.

16 Claims, 8 Drawing Sheets

(56) References Cited

U.S. PATENT DOCUMENTS

2008/0021336 A1* 1/2008 Dobak, III .................... 600/508
2008/0228089 A1* 9/2008 Cho et al. ..................... 600/485

FOREIGN PATENT DOCUMENTS

KR   1020030069744 A   8/2003
KR   100855043 B1      8/2008

* cited by examiner

ARM-FASTENING DEVICE FOR PULSE DIAGNOSIS, PULSE SENSOR, PULSE DIAGNOSIS APPARATUS COMPRISING THE DEVICE AND SENSOR, AND METHOD FOR MANUFACTURING PULSE SENSOR

RELATED APPLICATIONS

This application is a 35 U.S.C. 371 national stage filing from International Application No. PCT/KR2009/003077 filed Jun. 9, 2009 and claims priority to Korean Application No. 10-2008-0097830 filed Oct. 6, 2008 and Korean Application No. 10-2009-0020277 filed Mar. 10, 2009, the teachings of which are incorporated herein by reference.

TECHNICAL FIELD

The present invention relates to an arm-fastening device for a sphygmomanometer, a pulse sensor, sphygmomanometer apparatus including the arm-fastening device and the pulse sensor, and a method for fabricating the pulse sensor, and more particularly, to an arm-fastening device for a sphygmomanometer, a pulse sensor, sphygmomanometer apparatus including the arm-fastening device and the pulse sensor, and a method for fabricating the pulse sensor, in which a pulse of a person to be examined can be correctly measured in the state in which the person to be examined is a comfortable one when the pulse of the person to be examined is being measured.

BACKGROUND ART

When measuring a pulse using a pulse measuring device of the related art, the inner portion of an arm of a person to be examined is oriented upwards and maintained in a horizontal position. In this case, the brachioradialis and extensor carpi ulnaris of the wrist of the inside of the arm of the person to be examined are twisted, thereby pressing an artery or a vein, i.e. a blood vessel in the arm. Consequently, the pulse of the person to be examined may differ from the norm.

Oriental medical science requires a very precise pulse wave, and has diagnosed health conditions of persons to be examined based on the difference between such precise pulse waves.

Surgical operations of oriental medical science require a precise pulse wave like the above, yet it is difficult to correctly examine a pulse if a distorted pulse wave is provided as in the related art.

In addition, oriental medical science requires the person to be examined to remain comfortable when the pulse is examined.

If the person to be examined is tense, excited, or tired, it is difficult to examine the pulse correctly since the state of the pulse wave can change.

In the related art, since the pulse of a person is examined in the state in which the arm is twisted unlike the normal state, the person to be examined is uncomfortable. In addition, since the person may be tense, it becomes difficult to measure a correct pulse wave.

In addition, pulse measuring devices in the related art that use a cuff are devices that examine a pulse by disposing a sensor inside the cuff, mounting the cuff on the wrist using a Velcro tape, and injecting air into the cuff using a pump so that the sensor comes into contact with a portion from which a pulse is intended to be examined.

In such a pulse measuring device, the cuff is wound around the wrist and air is injected. This consequently presses the wrist in 360° directions, thereby causing congestion. In addition, the position of a pulse sensor changes in response to the cuff expanding, thereby making it impossible to measure a pulse wave in the intended position. A deformed pulse wave and deformed Korotkoff sound are detected, thereby making it difficult to measure a reliable pulse wave in a correct position.

Figure 1:
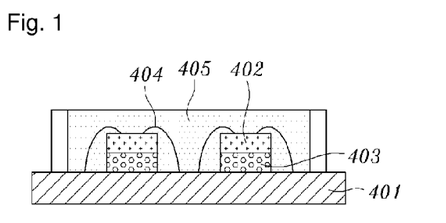
FIG. 1 is a cross-sectional view schematically showing a pulse sensor of the related art.

As shown in FIG. 1, a typical pulse sensor that is used in a pulse measuring device has a sensor chip 402 mounted on the upper end of a board 401. Here, the sensor chip 402 is fixedly mounted on the board 401 using a bonding material 403, and the sensor chip 402 and the board 401 are electrically connected to each other using bonding wires 404. Here, the bonding wires 404 are made of a material, such as Au or Al, and are mounted via wire bonding.

In addition, the sensor chip 402 and the bonding wires 404 are wrapped in a soft material 405 in order to protect the sensor chip 402 and the bonding wire 404.

However, this sensor chip 402 has problems, such as the bonding wires 404 being cut when the sensor chips 402 are frequently used, or a drawback of low durability, in which the bonding wires 404 are damaged by impact or vibrations. Since the entire module becomes defective if a defect occurs during processing, there is a problem of decreased productivity.

Furthermore, since the soft material is applied on the entire sensor chip, the area to which pressure is transferred is widely distributed, thereby causing a crosstalk phenomenon. Consequently, there are the constraints that it becomes impossible to correctly locate the pulse and difficult to produce correct data.

DISCLOSURE

Technical Problem

Accordingly, the present invention has been made keeping in mind the above problems, and is intended to provide a sphygmomanometer apparatus, in which an arm of a person to be examined can be comfortably placed without being twisted, and a pulse wave can be measured from a correct position corresponding to the oblique direction of a pulse-measuring position in the inner portion of the arm of the person to be examined, and a pulse sensor, which has increased durability thanks to bonding a sensor chip to a board via Face Down Bonding (FDC), and the sensor chip is increasingly sensitive to the pulse of the person to be examined while decreasing the crosstalk between sensor chips using holes formed in the board and a dam and gel disposed in the holes.

Technical Solution

In order to realize the foregoing objects, the present invention provides an arm-fastening device for a sphygmomanometer apparatus. The arm-fastening device includes an arm-fixing recess 13 capable of receiving a portion of an arm, in which a radial bone is located, at an incline such that an inner portion of the arm faces a person to be examined; an arm contact surface 12 provided in a lower portion of the arm-fixing recess 13, wherein the portion of an arm, in which a radial bone is located, is supposed to be placed in the arm contact surface 12; a body 11 having the arm contact surface 12 in an upper portion thereof; a main frame 1 provided in a lower end of the body 11 to fix the body 11; a horizontal rotation adjustment part 15 spaced apart from a front portion of the body 11 at a predetermined interval in an oblique direction, and fixed to the main frame 1 such that the horizontal rotation adjustment part 15 is horizontally rotatable;

and an arm-fixing unit 100 having a vertical rotation adjustment part 14, wherein the vertical rotation adjustment part 14 is fixedly provided on an upper end of the horizontal rotation adjustment part 15 such that the vertical rotation adjustment part 14 is vertically rotatable.

In addition, the sphygmomanometer apparatus of the present invention provides a sphygmomanometer apparatus. The sphygmomanometer apparatus includes a horizontal frame 22 distanced a predetermined interval from a side surface of an arm-fixing unit 100, wherein the horizontal frame 22 is elongated and fixed to a main frame 1 in a height direction; a horizontal control motor 20 fixed to a side surface of the horizontal frame 22 to provide a rotational force for a horizontal movement; a horizontal ball screw 24 fixedly connected to a rotation shaft of the horizontal control motor such that the horizontal ball screw 24 is rotatable; a horizontal motion guide 21 fixed to an upper end of the horizontal frame 22; a vertical frame 32 in contact with and connected to an upper portion of the horizontal frame 22, wherein both inner surfaces of a lower portion of the vertical frame 32 are fitted into the horizontal motion guide 21 such that the vertical frame 32 is reciprocally movable; a horizontal guide block 25 disposed on a lower inner surface of the vertical frame 32 and fitted into the horizontal motion guide 21; a horizontal ball screw nut 23 fixed to a lower portion of the vertical frame 32 and meshed with the horizontal ball screw 24; a vertical control motor 30 fixed to an upper end of the vertical frame 32, wherein a vertical control motor provides a rotational force for a vertical movement; a vertical ball screw 34 fixed to a rotation shaft of the vertical control motor 30 such that the vertical ball screw 34 is rotatable; a vertical movement guide 31 fixed to a front portion of the vertical frame 32; a vertical movement bracket 36 contacted with the front portion of the vertical frame 32 such that the vertical movement bracket 36 is vertically movable; a vertical guide block 35 provided on both inner portions of a surface of the vertical movement bracket 36 that faces the vertical movement guide 31, wherein the vertical guide block 35 is capable of being fitted into the vertical movement guide 31; a vertical ball screw nut 33 fixed to an inner portion of a side surface of the vertical movement bracket 36 that faces the vertical movement guide 31, the vertical ball screw nut 33 being meshed with the vertical ball screw 34; a large rotation motor 40 fixed to the vertical movement bracket 36 such that the large rotation motor 40 provides an angular rotational force; a large turntable 42 fixed to a rotation shaft of the large rotation motor 40 such that the large turntable 42 is angularly rotatable; a large rotation arm 41 fixed to the large turntable 42 such that the large rotation arm 41 is angularly rotatable with respect to the vertical movement bracket 36; a small rotation motor 50 fixed to a side surface of the large rotation arm 41 such that the small rotation motor 50 provides an angular rotational force; a small turntable 52 fixed to a rotation shaft of the small rotation motor 50 such that the small turntable 52 is angularly rotatable; a small rotation arm 61 fixed to the small turntable 52 such that the small rotation arm 61 is angularly rotatable with respect to the large rotation arm 41; an actuator 60 fixed to the small rotation arm 61 in a vertical lengthwise direction; and a sphygmomanometer unit 200 fixed to a lower end of the actuator 60, wherein the sphygmomanometer unit 200 has a pulse sensor 71 for converting a physical value of a pulse into an electrical signal, and is capable of pressing in an oblique direction.

Furthermore, the present invention provides a sphygmomanometer apparatus. The sphygmomanometer apparatus includes an arm-fixing recess 13 capable of receiving a portion of an arm, in which a radial bone is located, at an incline such that an inner portion of the arm faces a person to be examined; an arm contact surface 12 provided in a lower portion of the arm-fixing recess 13, wherein the portion of an arm, in which a radial bone is located, is supposed to be placed in the arm contact surface 12; a body 11 having the arm contact surface 12 in an upper portion thereof; a main frame 1 provided in a lower end of the body 11 to fix the body 11; a horizontal rotation adjustment part 15 spaced apart from a front portion of the body 11 at a predetermined interval in an oblique direction, and fixed to the main frame 1 such that the horizontal rotation adjustment part 15 is horizontally rotatable; and an arm-fixing unit 100 having a vertical rotation adjustment part 14, wherein the vertical rotation adjustment part 14 is fixedly provided on an upper end of the horizontal rotation adjustment part 15 such that the vertical rotation adjustment part 14 is vertically rotatable; a horizontal frame 22 distanced a predetermined interval from a side surface of an arm-fixing unit 100, wherein the horizontal frame 22 is elongated and fixed to a main frame 1 in a height direction; a horizontal control motor 20 fixed to a side surface of the horizontal frame 22 to provide a rotational force for a horizontal movement; a horizontal ball screw 24 fixedly connected to a rotation shaft of the horizontal control motor 20 such that the horizontal ball screw 24 is rotatable; a horizontal motion guide 21 fixed to an upper end of the horizontal frame 22; a vertical frame 32 in contact with and connected to an upper portion of the horizontal frame 22, wherein both inner surfaces of a lower portion of the vertical frame 32 are fitted into the horizontal motion guide 21 such that the vertical frame 32 is reciprocally movable; a horizontal guide block 25 disposed on a lower inner surface of the vertical frame 32 and fitted into the horizontal motion guide 21; a horizontal ball screw nut 23 fixed to a lower portion of the vertical frame 32 and meshed with the horizontal ball screw 24; a vertical control motor 30 fixed to an upper end of the vertical frame 32, wherein vertical control motor 30 provides a rotational force of a vertical movement; a vertical ball screw 34 fixed to a rotation shaft of the vertical control motor 30 such that the vertical ball screw 34 is rotatable; a vertical movement guide 31 fixed to a front portion of the vertical frame 32; a vertical movement bracket 36 in contact with the front portion of the vertical frame 32 such that the vertical movement bracket 36 is vertically movable; a vertical guide block 35 provided on both inner portions of a surface of the vertical movement bracket 36 that faces the vertical movement guide 31, wherein the vertical guide block 35 is capable of being fitted into the vertical movement guide 31; a vertical ball screw nut 33 fixed to an inner portion of a side surface of the vertical movement bracket 36 that faces the vertical movement guide 31, the vertical ball screw nut 33 being meshed with the vertical ball screw 34; a large rotation motor 40 fixed to the vertical movement bracket 36 such that the large rotation motor 40 provides an angular rotational force; a large turntable 42 fixed to a rotation shaft of the large rotation motor 40 such that the large turntable 42 is angularly rotatable; a large rotation arm 41 fixed to the large turntable 42 such that the large rotation arm 41 is angularly rotatable with respect to the vertical movement bracket 36; a small rotation motor 50 fixed to a side surface of the large rotation arm 41 such that the small rotation motor 50 provides an angular rotational force; a small turntable 52 fixed to a rotation shaft of the small rotation motor 50 such that the small turntable 52 is angularly rotatable; a small rotation arm 61 fixed to the small turntable 52 such that the small rotation arm 61 is angularly rotatable with respect to the large rotation arm 41; an actuator 60 fixed to the small rotation arm 61 in a vertical lengthwise direction; a sphygmomanometer unit 200 fixed to a lower end of the actuator 60, wherein the sphygmomanometer unit 200 has a pulse sensor 71 for converting a physical value of a pulse into an electrical signal, and is capable of pressing in an oblique direction; a central processing unit 500 fixedly provided in the main frame 1, wherein the central processing unit 1 processes an electrical signal output from the horizontal control motor 20, the vertical control motor 30, the large rotation motor 40, the small rotation motor 50, and the actuator; an image display unit 400 outputting a signal processed by the central processing unit 500; and an operating unit 300 allowing a processing signal of an operator to be input into the central processing unit 500.

Advantageous Effects

According to the sphygmomanometer apparatus of the present invention as described above, the arm-fixing device having a concave configuration is provided so that the arm of the person to be examined can be placed in a normal state in the arm-fixing device without being twisted. Consequently, this makes the person to be examined comfortable, thereby making it possible to measure a correct pulse wave from the person.

In addition, according to the sphygmomanometer apparatus of the present invention, even when the person to be examined casually places the arm in the arm-fastening device so that the inner portion of the wrist, the pulse-measuring position, is inclined with respect to the horizontal plane, the pulse sensor can be pressed in the oblique direction in a corresponding way so that it is oriented to be perpendicular to the incline. Consequently, a correct pulse wave can be measured without distortion.

Furthermore, the operator can compare pulse waves of both arms to each other by measuring the pulse waves using one sphygmomanometer apparatus.

In addition, according to the sphygmomanometer apparatus of the present invention, pulse waves can be measured from correct pulse-measuring positions, since it is possible to cope with various curvature characteristics of the surface of the skin of the arm of the person to be examined.

In the meantime, the pulse sensor of the present invention has increased durability thanks to the sensor chip being bonded to the board via FDB and the sensor chip has increased sensitivity to the pulse of the person to be examined while decreasing the crosstalk between sensor chips using holes formed in the board and a dam and gel disposed in the holes.

MODE FOR INVENTION

Reference will now be made in greater detail to exemplary embodiments of the present invention with reference to the accompanying drawings. Above all, reference should be made to the drawings, in which the same reference numerals and signs are used throughout the different drawings to designate the same or similar components. In the following description, it is to be noted that, when the functions of conventional elements and the detailed description of elements related with the present invention may make the gist of the present invention unclear, a detailed description of those elements will be omitted.

An arm-fastening device for a sphygmomanometer apparatus of the present invention is characterized by receiving an arm of a person to be examined at an incline so that a pulse can be correctly examined while the person is kept comfortable.

Figure 2:
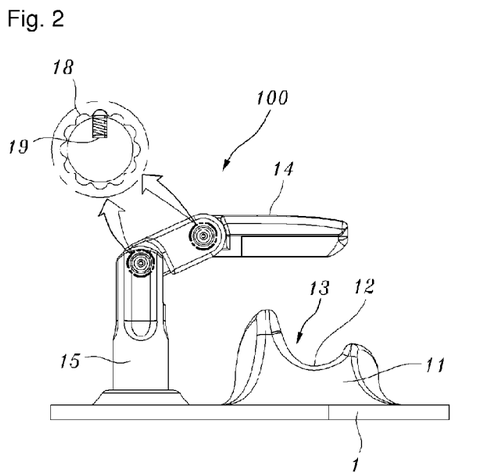
FIG. 2 is a front view showing an arm-fastening device for a sphygmomanometer apparatus according to an exemplary embodiment of the invention.

FIG. 2 is a front view showing an arm-fastening device for a sphygmomanometer apparatus of the invention.

Figure 3:
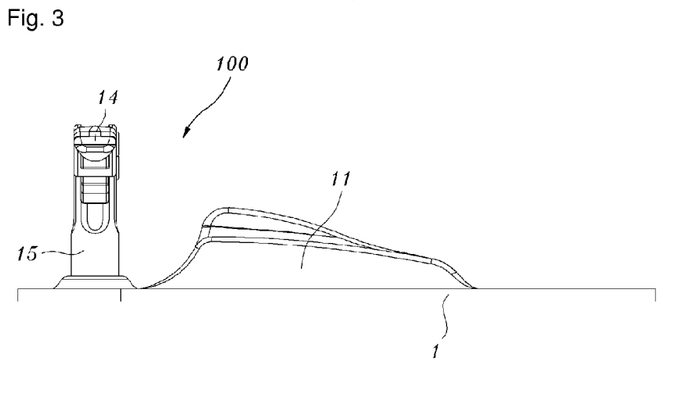
FIG. 3 is a right side elevation view of the arm-fastening device for a sphygmomanometer apparatus shown in FIG. 2.

FIG. 3 is a right side elevation view of the arm-fastening device for a sphygmomanometer apparatus of the invention.

Figure 4:
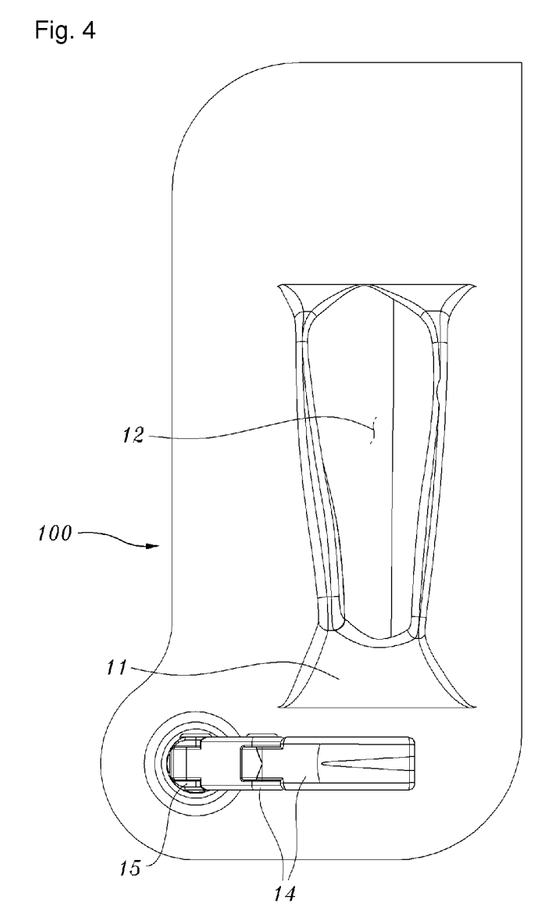
FIG. 4 is a top plan view of the arm-fastening device for a sphygmomanometer apparatus shown in FIG. 2.

FIG. 4 is a top plan view of the arm-fastening device for a sphygmomanometer apparatus of the invention.

Figure 5:
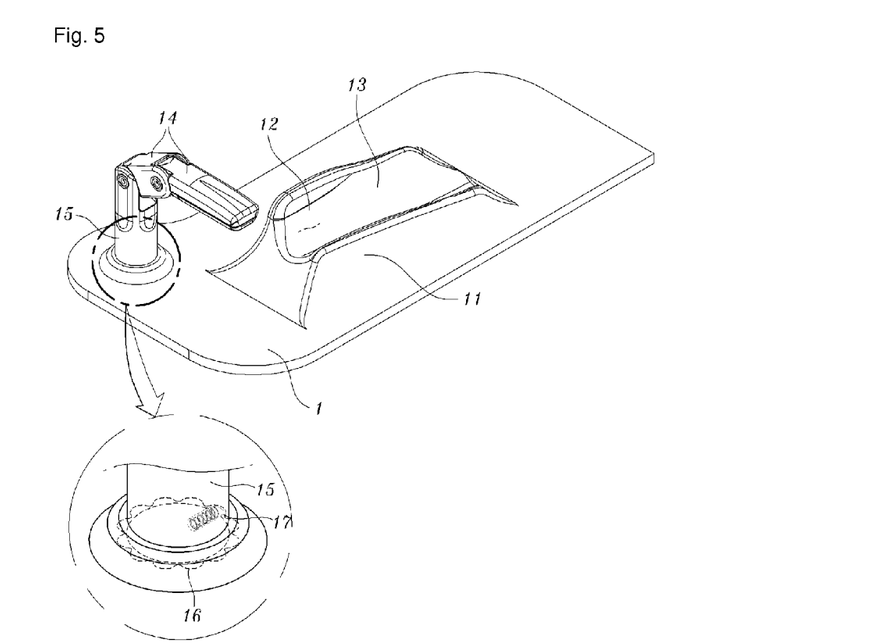
FIG. 5 is a perspective view of the arm-fastening device of a sphygmomanometer apparatus shown in FIG. 2.

FIG. 5 is a perspective view of the arm-fastening device of a sphygmomanometer apparatus of the invention.

The arm-fastening device for a sphygmomanometer apparatus of the invention has the following components and functions.

As shown in FIGS. 2, 3, 4, and 5, the arm-fastening device for a sphygmomanometer apparatus includes an arm-fixing recess 13, an arm contact surface 12, a body 11, a main frame 1, a horizontal rotation adjustment part 15, a vertical rotation adjustment part 14, a horizontal rotation adjustment recess 16, a horizontal rotation adjustment protrusion 17, a vertical rotation adjustment recess 18, and a vertical rotation adjustment protrusion 19.

The arm-fixing recess 13 is formed in a concave shape such that it can receive an arm at an incline so that the inner portion of the arm faces the person to be examined. Since the concave shape of the arm-fixing recess 13 corresponds to the curved surface of the skin, in which the radial bone of the arm is located, the person to be examined can comfortably place the arm in the arm-fixing recess 13. In the concave shape of the arm-fixing recess 13, it is preferred that the incline of the portion with which the rear portion of the arm is brought into contact be set to be steep and the incline of the portion with which the inner portion of the arm is brought into contact be set to be moderate so that the person to be examined can place his or her arm in the natural state. In addition, since the force of the person to be examined is applied to the rear portion of the arm, the arm-fixing recess 13 with which the rear portion of the arm is brought into contact is preferably reinforced by setting the height thereof to be higher than the portion with which the inner portion of the arm is brought into contact.

In addition, as shown in FIG. 5, it is preferred that the height of the arm-fixing recess 13 in the longitudinal direction be set such that the portion with which the wrist of the arm is brought into contact is higher than the portion with which the ankle is brought into contact. Through this, the arm of the person to be examined can be placed horizontally in its lengthwise direction.

As shown in FIG. 2, the arm contact surface 12 is provided in the lower portion of the arm-fixing recess 13, such that the portion of the arm of the person to be examined, in which the radial bone is located, is placed on the arm contact surface 12. It is preferred that one end of the arm contact surface 12 be tapered in order to comfortably receive the arm of the person to be examined.

The upper portion of the body 11 has the arm contact surface 12. The width of the body is preferably set such that it can receive the arm and correspond to shearing or vertical stress that is applied by the person to be examined. Accordingly, it is preferred that the size of the lower end of the body 11, which is fixed to the main frame 1, be greater than the size of the upper end.

The main frame 1 is fixed to the lower end of the body 11.

The horizontal rotation adjustment part 15 is positioned at a predetermined interval in the oblique direction from the front of the body 11, and is fixed such that it can horizontally rotate with respect to the main frame 1. Although the distance between the horizontal rotation adjustment part 15 and the body 11 preferably ranges between 50 mm to 100 mm in consideration of the distance from the wrist to the palm of an average person, this is not intended to be limiting. Thanks to the horizontal rotation of the horizontal rotation adjustment part 15, an operator can select a horizontal position that is suitable for examining a pulse.

The vertical rotation adjustment part 14 is fixedly provided on the upper end of the horizontal rotation adjustment part 15 such that it can rotate vertically. Thanks to the vertical rotation of the vertical rotation adjustment part 14, the operator can select a vertical position that is suitable for a pulse to be examined.

It is preferred that the portion of the vertical rotation adjustment part 14, which is not bound, have a concave shape having the form of fingers such that the person to be examined can grip it. However, this is not intended to be limiting.

Accordingly, the operator can select vertical and horizontal positions that are suitable for examining a pulse by manipulating the horizontal rotation adjustment part 15 and the vertical rotation adjustment part 14.

As shown in FIG. 5, the horizontal rotation adjustment part 15 can rotate to a predetermined angle via mesh engagement between the horizontal rotation adjustment recess 16 fixed to the main frame 1 and the horizontal rotation adjustment protrusion 17 fixed to the lower end of the horizontal rotation adjustment part 15. Consequently, the operator can rotate the horizontal rotation adjustment part 15 by a predetermined angle.

In addition, thanks to the binding force of the mesh engagement between the horizontal rotation adjustment recess 16 and the horizontal rotation adjustment protrusion 17, the horizontal rotation adjustment part 15 is prevented from excessively rotating unless a force exceeding the binding force is applied.

As shown in FIG. 2, thanks to the mesh engagement between the vertical rotation adjustment recess 18 fixed to the upper end of the horizontal rotation adjustment part 15 and the vertical rotation adjustment protrusion 19 fixed to the lower end of the vertical rotation adjustment part 14, the operator can rotate the vertical rotation adjustment part 14 by a predetermined angle, and the vertical rotation adjustment part 14 can be prevented from spinning idly due to the binding force of the mesh engagement between the vertical rotation adjustment recess 18 and the vertical rotation adjustment protrusion 19.

The method of operating an arm-fixing unit 100 of the invention is as follows:

The operator places the portion of an arm, in which the radial bone is located, in the arm-fixing recess 13. Here, due to the concave shape of the arm-fixing recess 13, the inner portion of the arm faces a person to be examined, and the arm is placed at an incline while in contact with the arm contact surface 12. Afterwards, the operator selects horizontal and vertical positions that are suitable for examining a pulse by grasping and rotating a handle on one end of the horizontal rotation adjustment part 15. When the horizontal rotation adjustment part 15 and the vertical rotation adjustment part 14 rotate, the horizontal rotation adjustment part 15 is forced to horizontally rotate at a predetermined rate due to the force of the engagement between the horizontal rotation adjustment protrusion 17 and horizontal rotation adjustment recess 16, which are below the horizontal rotation adjustment part 15, and the vertical rotation adjustment part 14 is made to rotate to a predetermined angle due to the force of the engagement between the vertical rotation adjustment protrusion 19 and the vertical rotation adjustment recess 18, which are provided on one portion of the vertical rotation adjustment part 14. Therefore, the horizontal position and the vertical position selected by the operator do not change unless a force exceeding the force of the engagement is applied.

A sphygmomanometer unit for a sphygmomanometer apparatus of the present invention is characterized by moving a pulse sensor in response to an arm of the person to be examined even if the arm is placed at an incline, such that the pulse sensor is oriented perpendicular to the oblique direction of the inner portion of an arm of a person to be examined, in order to press the pulse-measuring position in the oblique direction.

Figure 6:
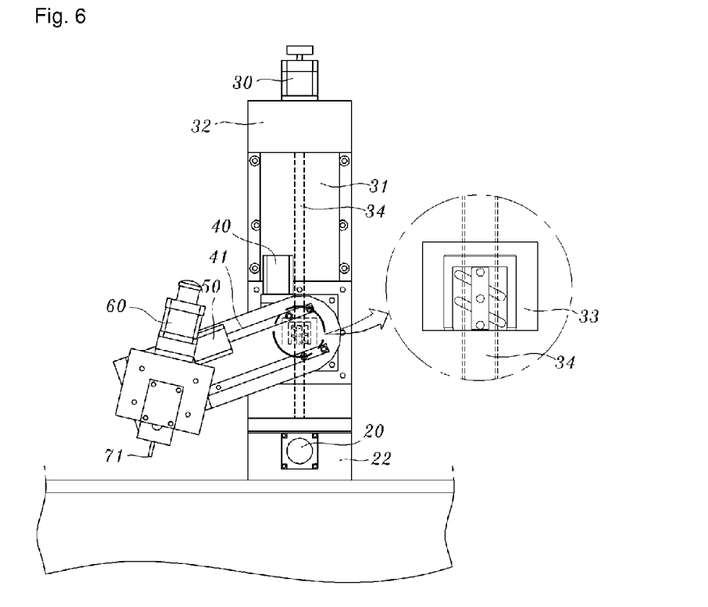
FIG. 6 is a front elevation view of a sphygmomanometer unit for a sphygmomanometer apparatus according to an exemplary embodiment of the invention.

FIG. 6 is a front elevation view of a sphygmomanometer unit for a sphygmomanometer apparatus of the invention.

Figure 7:
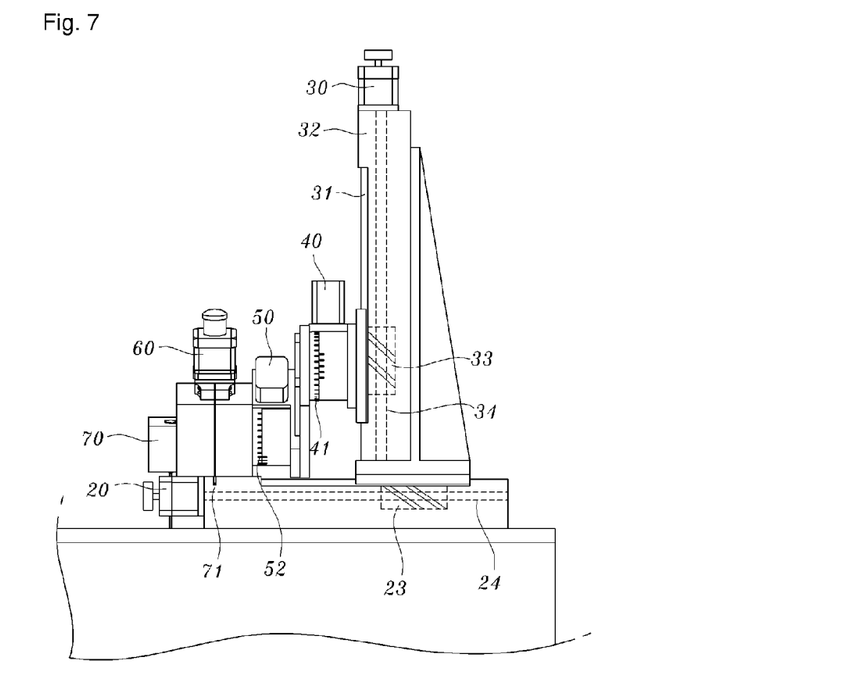
FIG. 7 is a right side elevation view of the sphygmomanometer unit of a sphygmomanometer apparatus shown in FIG. 6.

FIG. 7 is a right side elevation view of the sphygmomanometer unit for a sphygmomanometer apparatus of the invention.

Figure 8:
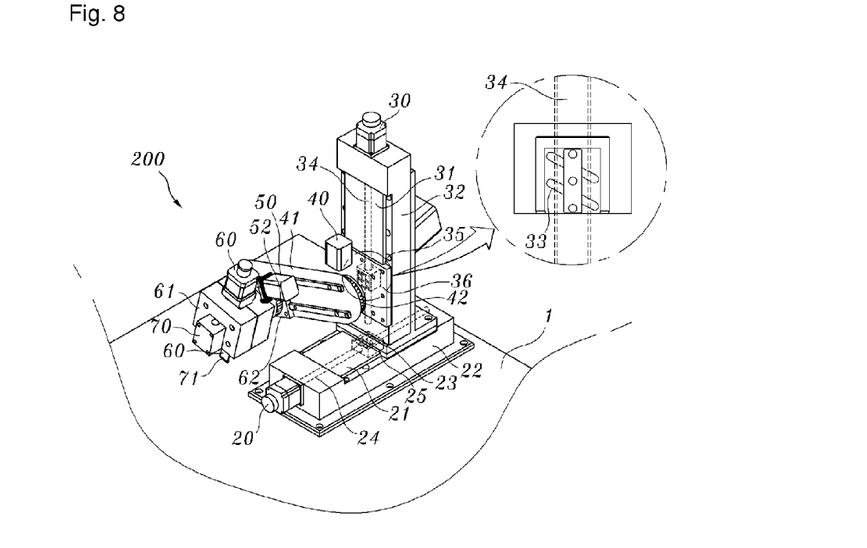
FIG. 8 is a perspective view of the sphygmomanometer unit of a sphygmomanometer apparatus shown in FIG. 6.

FIG. 8 is a perspective view of the sphygmomanometer unit for a sphygmomanometer apparatus of the invention.

The sphygmomanometer unit for a sphygmomanometer apparatus of the invention has the following components and functions thereof.

As shown in FIGS. 6, 7, and 8, the sphygmomanometer unit for a sphygmomanometer apparatus of the invention includes a horizontal frame 22, a horizontal control motor 20, a horizontal ball screw 24, a horizontal motion guide 21, a vertical frame 32, a horizontal guide block 25, a horizontal ball screw nut 23, a vertical control motor 30, a vertical ball screw 34, a vertical movement guide 31, a vertical movement bracket 36, a vertical guide block 35, a vertical ball screw nut 33, a large rotation motor 40, a large turntable 42, a large rotation arm 41, a small rotation motor 50, a small turntable 52, a small rotation arm 61, an actuator 60, and a pulse sensor 71.

As shown in FIGS. 6, 7, and 8, the horizontal frame 22 is distanced a predetermined interval from the side surface of the arm-fixing unit 100, and is elongated and fixed to the main frame 1 in the height direction. The horizontal frame 22 is a frame that allows the pulse sensor 71 to move in the lengthwise direction of an arm of a person to be examined, and is preferably provided to be longer than the length of the arm contact surface 12 of the arm-fastening device 10.

The horizontal control motor 20 is fixedly provided on the side surface of the horizontal frame 22, and provides a rotational force for a horizontal movement. Among motors of the invention, the horizontal control motor 20 provides a rotational force that moves a great mass. Thus, it is preferred that the horizontal control motor be a motor having a very large output.

The horizontal ball screw 24 is fixedly connected to the rotation shaft of the horizontal control motor 20 such that it can rotate. The horizontal ball screw 24 is meshed with the horizontal ball screw nut 23, which is fixed to the lower portion of the vertical frame 32. Due to this configuration, when the shaft of the horizontal control motor 20 rotates, the horizontal ball screw 24 rotates, and the vertical frame 32 fixed to the lower portion of the horizontal ball screw nut 23 moves horizontally. Here, the horizontal guide block 25, which is provided in the inner surface of the lower portion of the vertical frame 32, is fitted into the horizontal motion guide 21, which is fixed to the upper end of the horizontal frame 22, so that the vertical frame 32 reciprocally moves along the horizontal motion guide 21.

The vertical control motor 30 is fixedly provided on the upper end of the vertical frame 32, and provides a rotational force for a vertical movement. It is preferred that the height of the vertical frame 32 be provided such that it forms a sufficient space so that the path of motion of the person to be examined is not obstructed when he/she is placing the arm on the arm-fixing unit 100. The vertical ball screw 34 is fixedly connected to the rotation shaft of the vertical control motor 30 such that it can rotate.

The vertical ball screw 34 is meshed with the vertical ball screw nut 33, which is fixed to the inner surface of the vertical movement bracket 36. Due to this configuration, when the shaft of the vertical control motor 30 rotates, the vertical ball screw 34 rotates, and the vertical movement bracket 36, which is fixed to the inner surface of the vertical ball screw nut 33, moves vertically. As the vertical guide block 35 provided on both sides of the inner surface of the vertical movement bracket 36 is fitted into the vertical movement guide 31, which is fixed to the front surface of the vertical frame 32, the large rotation arm 41 vertically moves along the vertical movement guide 31.

The large rotation motor 40 is fixed to the vertical movement bracket 36, and provides an angular rotational force to the large turntable 42.

The large rotation arm 41 is fixedly connected to the large turntable 42, such that it can angularly rotate with respect to the vertical movement bracket 36.

It is preferred that the length of the large rotation arm 41 range from 150 mm to 250 mm in consideration of the interval between the arm-fixing unit 100 and the horizontal frame 22. However, this is not intended to be limiting.

The large turntable 42 is fixedly connected to the rotation shaft of the large rotation motor 40, and provides an angular rotational force to the large rotation arm 41.

Due to the configuration of the large rotation motor 40, as soon as the large rotation motor 40 rotates, the large turntable 42 rotates. Here, the large rotation arm 41, which is fixed to the large turntable 42, also rotates. The angle of rotation of the large rotation arm 41 is preferably symmetrical to the right and left with respect to the vertical frame 32 so that pulses can be examined when both hands of the person to be examined are placed on the right and left portions of the sphygmomanometer unit 200.

The small rotation motor 50 is fixed adjacent to the large rotation arm 41, and provides an angular rotational force to the small rotation arm 61.

The small turntable 52 is fixedly connected to the rotation shaft of the small rotation motor 50 such that it can angularly rotate.

The small rotation arm 61 is fixed to the small turntable 52, such that it can angularly rotate with respect to the large rotation arm 41.

Due to the configuration of the small rotation motor 50, as soon as the small rotation motor 50 rotates, the small turntable 52 rotates, and the small rotation arm 61 fixed to the small turntable 52 also rotates.

The actuator 60 is vertically fixed to the small rotation arm 61 in the height direction.

The operation of the actuator 60 is required to be precise, since it finally brings the pulse sensor 71 into contact with the skin of the person to be examined.

Therefore, it is preferred that the actuator 60, which is operated by hydraulic pressure, be used in order to precisely operate the pulse sensor 71, which is provided on the lower end of the actuator 60.

The pulse sensor 71 is fixedly provided on the actuator 60, and converts a physical value of a pulse into an electrical signal.

Figure 9:
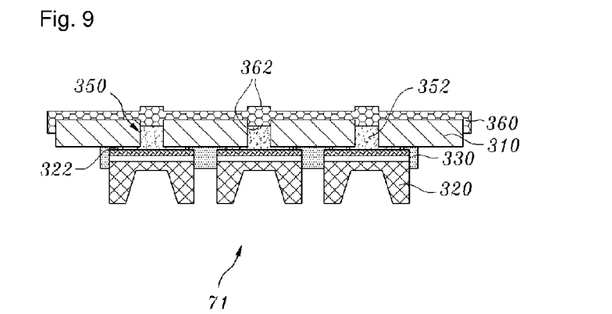
FIG. 9 is a cross-sectional view schematically showing a pulse sensor according to an exemplary embodiment in the sphygmomanometer unit of the sphygmomanometer apparatus shown in FIG. 6.
Figure 10:
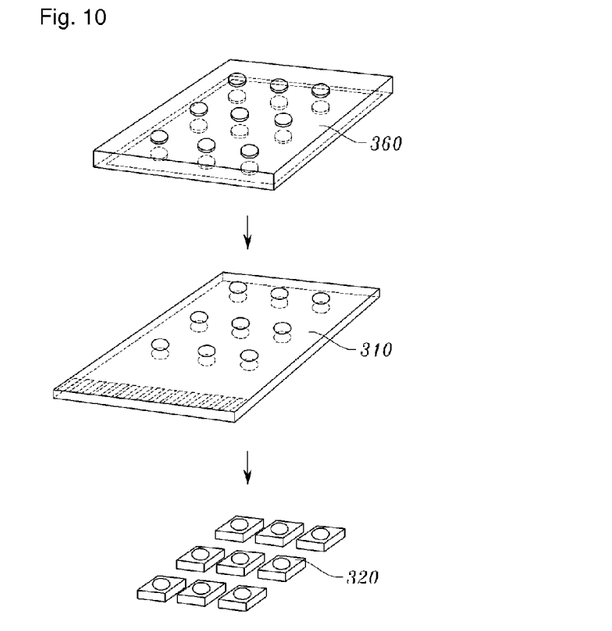
FIG. 10 is an exploded perspective view schematically showing the pulse sensor shown in FIG. 9.

As shown in FIGS. 9 and 10, the pulse sensor 71 includes a board 310, a sensor chip 320, which is attached to one side of the board 310 and is electrically connected thereto, a pad 360 attached to the other side of the board 310, and pressure transferring members 350 buried in the board 310.

The board 310 has one or more first holes 312, in which the pressure transferring members 350 are contained as will be described later.

The board 310 configured as above is arranged between the sensor chip 320 and the person to be examined in order to prevent the sensor chip 320 from being damaged while a pulse is being examined. In other words, unlike the related art in which the sensor chip is arranged adjacent to the person to be examined, the board 310 can prevent the sensor chip 320 from being damaged as the frequency of use of the pulse sensor 71 increases.

In addition, the sensor chips 320 are attached to one surface of the board 310 so that the first holes 312 of the board 310 are closed. That is, the sensor chip 320 is configured such that it can effectively receive the pressure transferred via the pressure transferring members 350 provided inside the first holes 312. Of course, the sensor chip 320 is electrically connected because it is in the state of being in contact with the board 310

Here, it is preferred that a plurality of first holes 312 have been formed in the board 310 and are spaced apart from each other at regular intervals, and a plurality of sensor chips 320 corresponding to the plurality of first holes 312 are fixedly attached to the circumference of the first holes 312. Furthermore, it is more preferable that sensor chips 320 be arranged in a 3-by-3 array in orthogonal directions such that they properly correspond to the range of the pulse of the person to be examined.

Here, an epoxy 330 can be applied on one surface of the board 310, between the side portions of the sensor chips 320, and between the sensor chips 320 so the sensor chips 320 are fixed to the board 310 and to each other.

As the epoxy 330, which is applied as above, cures, the sensor chips 320 are securely fastened to the board 310 while the sensor chips 320 are securely fastened to each other.

Of course, a fixing member that fixes the components to each other is not limited to epoxy 330, and any material can be employed as long as it has adhesion that increases the fixing force of the components.

In the meantime, the pad 360 is the portion with which the pulse of the user is in contact, and is attached to the other surface of the board 310 so that the first holes 312 of the board 310 are closed.

Here, the pad 360 has pressing portions 362 that protrude from one and the other surfaces of the board 310, which correspond to the first holes 312. The pressing portions 362 are positioned inside the first holes 312 such that they can move up and down inside the first holes 312 in response to the pulsation of the person to be examined.

Due to the pressing portions 362 of the pad 360, pressure in response to the pulsation of the person to be examined can be effectively transferred to the sensor chip 320. That is, the pressure of the pulsation of the person to be examined is transferred to the pressure transferring members 350, which are provided inside the first holes 312, via the pressing portions 362, and the pressure transferring members 350 transfer the pressure to the sensor chips 320.

In addition, the pressing portions 362 are configured such that the person to be examined can correctly locate the pulse on the pressing portions 362. Consequently, it becomes possible to produce correct data from the pulse.

Here, the pressure transferring members 350 are provided inside the first holes 312 so that input signals that the pad 360 receives are effectively transferred to the sensor chips 320, and the pressure transferring members 350 are preferably a gel 352, which is disposed in the first holes 312.

Thanks to the gel 352, the board 310, the sensor chips 320, and the pad 360, which are in contact with the gel 352, can be prevented from being damaged by friction, and an input signal that the pad 360 receives can be effectively transferred to the sensor chips 320. Thereby, the sensitivity of the sensor chip 320 to the pulse of the person to be examined can be increased.

Furthermore, the pressure of the pulse is not transferred through the board 310, but a local input transfer path is formed through the first hole 312. This can consequently minimize the crosstalk between the sensor chips 320. In addition, the gel 352 is preferably a silicone gel.

Although not shown in the figures, the pressure transferring members 350 can include sticks, which are buried in the gel 352 and are arranged lengthwise along the first holes 312.

The pulse sensor 71 configured as above can further minimize crosstalk thanks to the sticks that effectively transfer pressure.

In addition, since the sticks are made of a hard material and are wrapped in the gel 352, the pulse sensor 71 can more effectively transfer the input signals while having the effect of preventing the other components from being damaged by friction because of the gel 352.

Here, the sticks is provided inside the gel 352 in the first hole 312, and the upper end of the stick can be made of a soft material. The pulse sensor 71 does not have a separate pad, and the upper end of the stick functions as the pad.

As such, the stick having the upper end, which is exposed to the outside and is made of a soft material, can almost perfectly remove the interference between the sensors, that is, crosstalk, thereby increasing precision pertaining to the transfer of pressure.

Of course, this is not intended to limit the structure of the stick. Rather, the stick can have any shape or structure as long as it can effectively transfer input signals using the gel.

Furthermore, the sensor chip 320 includes a plurality of solder balls 322 attached to one surface of the board 310. The solder balls 322 protrude from the circumference of the surface corresponding to the board 310. The solder balls 322 are intended to electrically connect the board 310 and the sensor chips 320 to each other, and to allow the gel 352 to be disposed therebetween.

Consequently, the gel 352 disposed in the first hole 312 also fills the space between one surface of the board 310 and the sensor chip 320, thereby improving the transfer of input signals.

Figure 11:
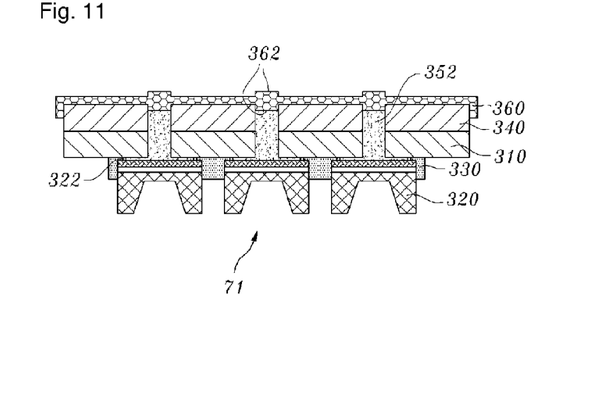
FIG. 11 is a cross-sectional view schematically showing a pulse sensor according to another exemplary embodiment in a sphygmomanometer unit of the sphygmomanometer apparatus shown in FIG. 5.
Figure 12:
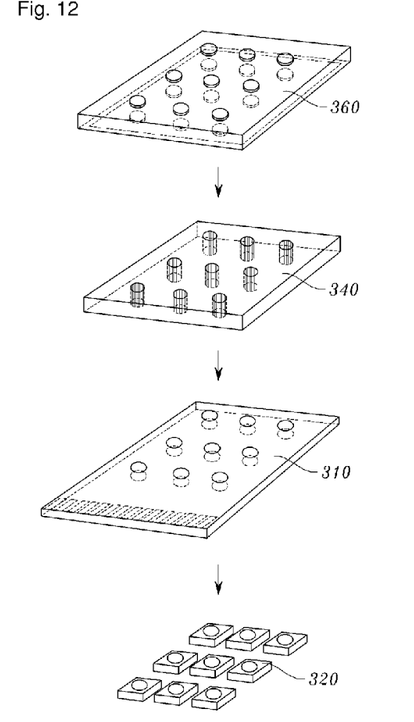
FIG. 12 is an exploded perspective view schematically showing the pulse sensor shown in FIG. 11.

In the meantime, as shown in FIGS. 11 and 12, the pulse sensor 71 configured as above may also include a dam 340 disposed between the board 310 and the pad 360 as another embodiment.

The dam 340 is disposed between the board 310 and the 360 such that second holes 342 communicate with the first holes 312, and is attached to the board 310 and the pad 360. Of course, the gel 352 of the pressure transferring member 350 is disposed between the first holes 312 and the second holes 342.

In addition, although not shown in the figures, the pressure transferring member 350 can include sticks, which are buried in the gel 352 and are arranged lengthwise along the first holes 342.

As such, the dam 340 has a more effective function in order to minimize the crosstalk between the sensor chips 320. Specifically, the pulse sensor 71 has the effect of minimizing the crosstalk, which is caused by a localized input transfer path defined by the first holes 312 and the pressure transferring members 350 inside the holes 312, and can enhance this effect by further including the dam 340 made of a hard material.

The pulse sensor 71 of the invention can increase the durability by bonding between the sensor chip 320 and the board 310 using Face Down Bonding (FDB) as above, decrease the crosstalk between the sensor chips 320 using the holes formed in the board 310 and the dam 340 and the gel 352 disposed in the holes, and increase the sensitivity of the sensor chip 320 to the pulsation of the person to be examined.

In addition, a laser point unit 70 shown in FIG. 8 has a function of indicating the position of pulsation in the wrist of the person to be examined by pointing to it. Consequently, the operator can correctly locate the pulse sensor 71 on the position of pulsation in the wrist of the person to be examined. The position pointed by the laser pointing unit 70 is set to match the position in which the pulse sensor 71 is finally brought into contact with the skin of person to be examined. Details thereof will be described with respect to the method of operating the sphygmomanometer unit 200.

The sphygmomanometer unit 200 of the present invention will be operated as follows.

The operator indicates a pulse-measuring position after finding it.

The vertical frame 32 is horizontally moved by rotating the horizontal control motor 20 of the sphygmomanometer unit 200 while the vertical movement bracket 36 is vertically moved up and down by rotating the vertical control motor 30.

At the same time, the large rotation arm 41 is rotated using the large rotation motor 40 so that the pulse sensor 71 is located in an approximate position above the pulse-measuring position, as is indicated by the operator.

Afterwards, the small rotation motor 50 is rotated so that the actuator 60, which is vertically provided in the small rotation arm 61 in the height direction, is oriented perpendicular to the incline of the inner portion of the wrist of the person to be examined.

Here, it is confirmed whether or not the pulse sensor 71 is correctly located above the pulse-measuring position, as is indicated by the operator, using a laser beam that is linearly radiated in an oblique direction by the laser pointing unit 70.

If the portion that is pointed to by the laser pointing unit 70 does not indicate the pulse-measuring position, as is indicated by the operator, the portion that is pointed to by the laser is set to point to the position, per the instruction of the operator, by compensating for errors in the horizontal control motor 20, the vertical control motor 30, the large rotation motor 40, and the small rotation motor 50, so that the pulse sensor 71 is correctly located above the pulse-measuring position.

Afterwards, the pulse sensor 71, which is fixed to the lower end of the actuator 60, is moved down following the operation of the actuator 60 to come into contact with the inner portion of the wrist of the person to be examined while pressing it.

If the wrist of the person to be examined is inclined, the actuator 60, which is fixed to the small rotation motor 50, is oriented perpendicular to the incline of the wrist by rotating the small rotation motor 50. The pulse sensor 71 can be moved in the oblique direction by raising and descending the pulse sensor 71, which is fixed to the lower end of the actuator 60. Then, the pulse sensor 71 comes into contact with the pulse-measuring position in the inner portion of the wrist of the person to be examined while it is pressed in an oblique direction.

The sphygmomanometer apparatus of the present invention is characterized in that it can locate the pulse sensor 71 in a correct pulse-measuring position, as indicated by an operator, examine a correct pulse even if the pulse-measuring position of a person to be examined is inclined, and compare pulses from both arms of the person to be examined because the pulses are measured using a large rotation arm.

Figure 13:
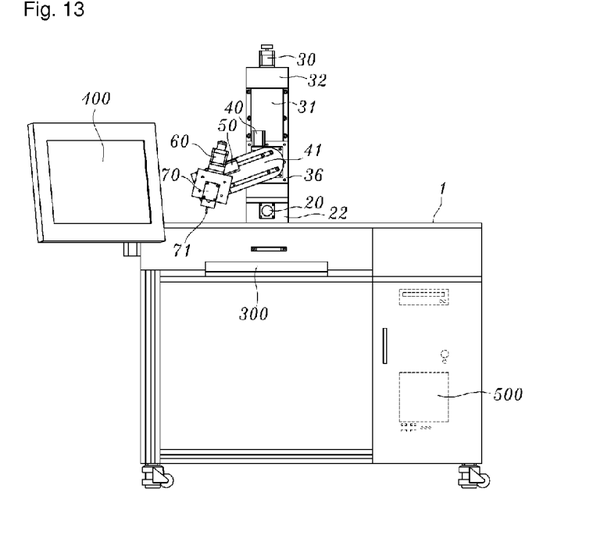
FIG. 13 is a front elevation view showing a sphygmomanometer apparatus according to an exemplary embodiment of the present invention.

FIG. 13 is a front elevation view showing a sphygmomanometer apparatus of the present invention.

Figure 14:
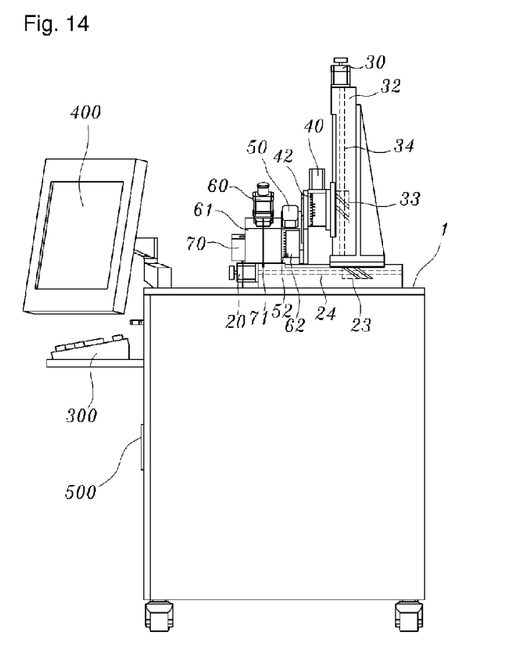
FIG. 14 is a right elevation view of the sphygmomanometer apparatus shown in FIG. 13.

FIG. 14 is a right elevation view of the sphygmomanometer apparatus of the present invention.

Figure 15:
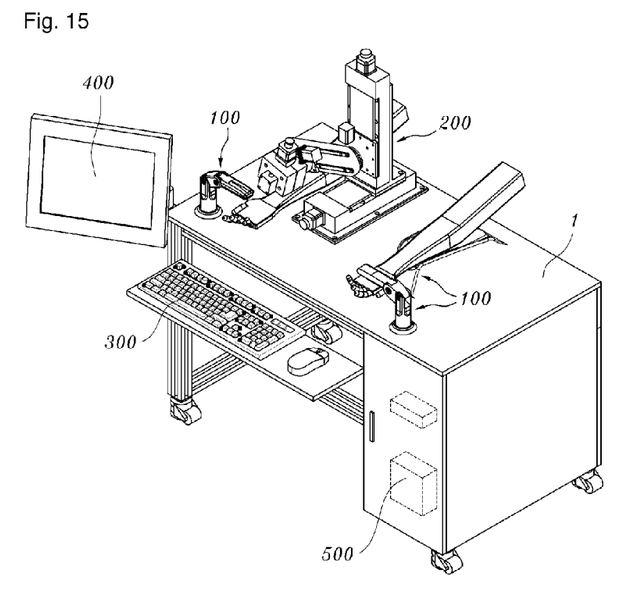
FIG. 15 is a perspective view of the sphygmomanometer apparatus according to an exemplary embodiment of the present invention, which can examine the pulses of both arms at the same time.

FIG. 15 is a perspective view of the sphygmomanometer apparatus of the present invention, which can examine pulses from both arms at the same time.

As shown in FIGS. 13, 14, and 15, the sphygmomanometer apparatus of the invention includes a main frame 1, an arm-fixing unit 100, a sphygmomanometer unit 200, a Central Processing Unit (CPU) 500, an image display unit 400, and an operating unit 300.

As shown in FIGS. 13, 14, and 15, the sphygmomanometer unit 200 is fixed to the upper end of the main frame 1.

As shown in FIG. 15, the arm-fixing unit 100 is fixed to the main frame 1 while spaced apart from the side surface of the sphygmomanometer unit 200 in an oblique direction.

It is preferred that the distance in the oblique direction between the sphygmomanometer unit 200 and the arm-fixing unit 100 range between 200 mm and 300 mm. However, this is not intended to be limiting.

The CPU 500 is fixedly provided in the main frame 1, and can process electrical signals that are input to and output from the horizontal control motor 20, the vertical control motor 30, the large rotation motor 40, the small rotation motor 50, and the actuator 60.

The image display unit 400 is fixed to the main frame 1, and is connected to the CPU 500 so that it outputs signals that are processed by the CPU 500.

The operating unit 300 is connected to the CPU 500, and can input process signals of the operator to the CPU 500.

The method of operating the sphygmomanometer apparatus of the invention is as follows.

The wrist of the person to be examined is placed on the arm-fixing unit 100.

The operator indicates a pulse-measuring position of the wrist of the person to be examined after finding it.

The operator inputs signals of the pulse-measuring position to the operating unit 300. The signals are sent to the CPU 500, which in turn locates the pulse sensor 71 vertically above the wrist of the person to be examined that has been put on an incline by operating the horizontal control motor 20, the vertical control motor 30, the large rotation motor 40, the small rotation motor 50, and the actuator 60.

A position signal is sent to the operating unit 300 so that the point of a laser beam, which is radiated from the laser pointing unit 70, is located on the pulse-measuring position, as indicated by the operator. This signal is processed by the CPU 500 to operate the respective motors, so that the point of the laser beam, which is radiated from the laser pointing unit 70, is located on the pulse-measuring position of the person to be examined.

Afterwards, the pulse sensor 71 is brought into contact with the pulse-measuring position of the wrist of the person to be examined by operating the actuator 60, signals output from the pulse sensor 71 are sent to the CPU 500, and pulse signals are output by the image display unit 400, which is connected to the CPU 500.

In addition, as shown in FIG. 15, even in the case in which the arms of the person to be examined are placed on both sides of the sphygmomanometer unit 200, pulses can be examined first from one arm and then from the other arm by rotating the large rotation arm 41.

Although the sphygmomanometer apparatus of the present invention has been described with reference to the illustrated drawings, the invention is by no means limited to the embodiments and drawings disclosed herein. Rather, various changes can be made by a person having ordinary skill in the art without departing from the scope of the invention.

Figure 17:
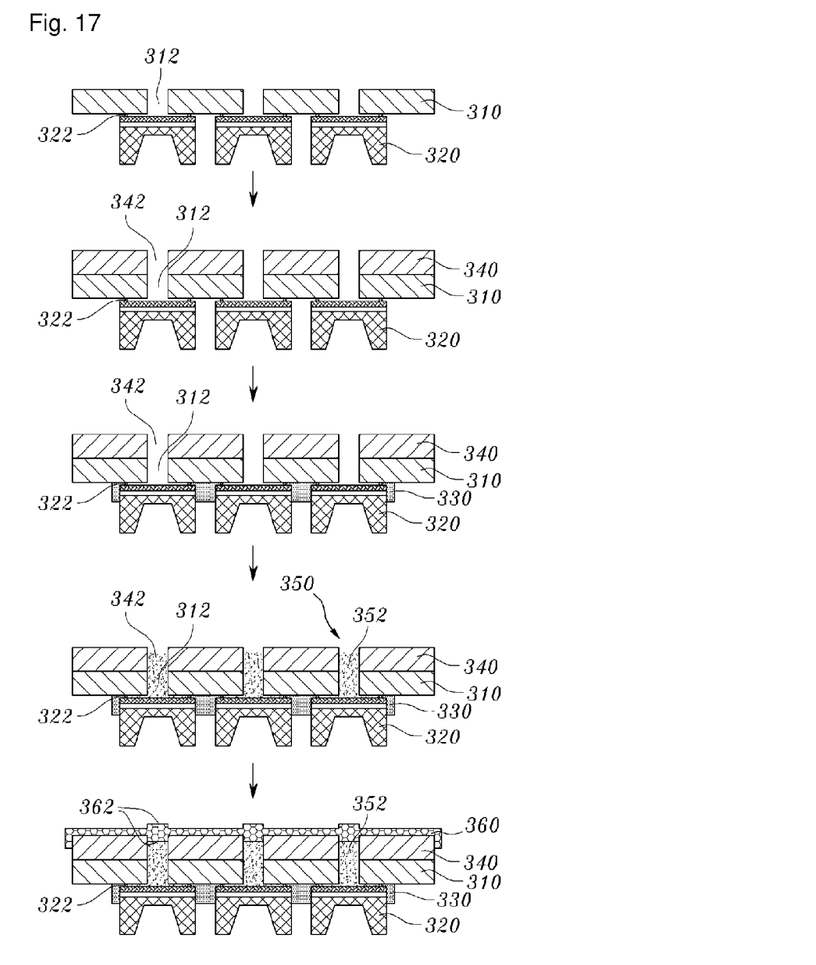
FIG. 17 is a view showing a method for fabricating the pulse sensor shown in FIG. 11.

In the meantime, a method for fabricating a pulse sensor 71 of the sphygmomanometer apparatus of the invention is described with reference to FIG. 17.

First, a sensor chip 320 is prepared in order to fabricate the pulse sensor 71. The method of fabricating a sensor chip 320 is described with reference to FIG. 16. First, aluminum oxide produced on one surface of the sensor chip 320 is removed, and then a zinc plating layer 325 is formed by zinc plating. The zinc plating is performed to substitute nickel with zinc, since nickel cannot be plated on aluminum.

Figure 16:
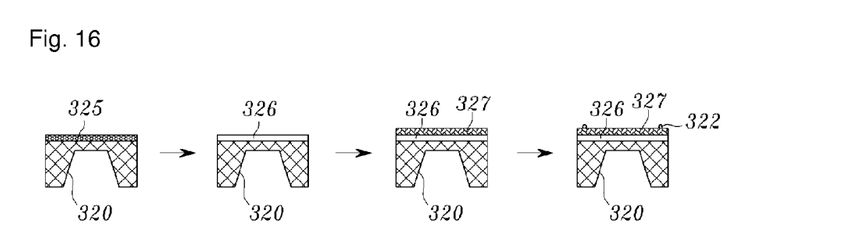
FIG. 16 is a view showing a method for fabricating a sensor chip of the pulse sensor shown in FIG. 9.

Afterwards, the zinc plating layer 325 is removed, and nickel plating is performed, thereby forming a nickel plating layer 326. The nickel plating layer 326 serves to prevent intermetallic diffusion of solder, which is used for the above-described solder balls 322. Here, it is preferred that the thickness of the nickel plating layer 326 range from 1 μm to 3 μm because of intermetallic diffusion of the solder.

Thereafter, to prevent the nickel plating layer 326 from being oxidized, gold is plated on the nickel plating layer 326, thus forming a gold plating layer 327.

The present invention relates to an arm-fastening device for a pulse diagnosis, a pulse sensor, a pulse diagnosis apparatus comprising the device and sensor, and a method for manufacturing the pulse sensor. The arm-fastening device (100) comprises: an arm-fastening groove (13) which declines and holds the radius of an arm to hold the inner side of the arm toward a user; an arm contact surface (12) installed at the lower side of the arm-fastening groove (13) in which the radius of a user's arm can be placed; a body part (11) having the arm contact surface at the upper portion thereof; a main frame (1) installed at the lower end of the body part (11) which fastens the body part (11); a horizontal rotation control part (15) which is separated from the front side of the body part (11) in a diagonal direction at a specific interval and is fixed on the main frame to enable horizontal rotation; and a vertical rotation control part (14) which is fixed at the upper end of the horizontal rotation control part (15) to enable vertical rotation. Also, a pulse sensor comprises: a substrate (310) with at least one first hole (312); a sensor chip (320) attached at one side of the substrate (310) to electrically connect to the substrate (310) when the first hole (312) of the substrate (310) is closed; a pad (360) which is attached at the other side of the substrate (310) to close the first hole (312) of the substrate (310), in which a user's pulse is contacted; and a built-in pressure delivery member (350) in the first hole (312) of the substrate (310) to deliver a pressure signal through the pad (360) to the sensor chip (320). In addition, the pulse diagnosis apparatus comprises: a horizontal frame (22) which is separated from the side of the arm-fastening part (100) by a specific interval and fixed on the main frame (1) upwardly; a horizontal control motor (20) which is fixed on the side of the horizontal frame (22) and provides horizontal torque; a horizontal ball screw (24) which is fixed to the rotation shaft of the horizontal control motor (20) to allow rotation; a horizontal movement guide (21) fixed at the upper end of the horizontal frame (22); a vertical frame (32) which is connected to the upper side of the horizontal frame (22) and of which both sides of the lower inner side is fitted to the horizontal movement guide (21) in order to enable forward and backward movement; a horizontal guide block (25) installed at the inner side of the lower vertical frame (32) which is inserted into the horizontal movement guide (21); a horizontal ball screw nut (23) which is fixed at the lower side of the vertical frame (32) and coupled with the horizontal ball screw (24); a vertical control motor (30) which is fixed to the upper end of the vertical frame (32) and provides vertical torque; a vertical ball screw (34) which is fixed to the rotation shaft of the vertical control motor (30) to allow rotation; a vertical movement guide (31) fixed on the front of the vertical frame (32); an upward and downward movement bracket (36) which contacts with the front of the vertical frame (32) and enables upward and downward movement; a vertical guide block (35) installed at both inner sides of the vertical movement guide (31) side of the upward and downward movement bracket (36) and can be inserted into the vertical movement guide (31); a vertical ball screw nut (33) which is fixed to the inner side of the vertical movement guide (31) of the upward and downward movement bracket (36) and coupled to the vertical ball screw (34); a large rotation motor (40) fixed to the upward and downward movement bracket (36) to provide angular rotation force; a large rotation board (42) which is fixed at the rotation shaft of the large rotation motor (40) to allow angular rotation; a large rotation arm (41) fixed on the large rotation board (42) and connected to the upward and downward movement bracket (36) to enable angular rotation therearound; a small rotation motor (50) fixed on the side of the large rotation arm (41) to provide angular torque; a small rotation board (52) which is fixed at the rotation shaft of the small rotation motor (50) to allow angular rotation; a small rotation arm (61) fixed on the small rotation board (52) and connected to the large rotation arm (41) to enable angular rotation therearound; an actuator (60) which is fixed to the small rotation arm (61) in a vertically longitudinal direction; and a pulse diagnosis part (200) which has the pulse sensor (71) which is fixed at the lower end of the actuator (60) and converts the physical value of the pulse wave to an electrical signal to pressurizes in a diagonal direction.

Finally, flux is applied on the gold plating layer 327, and a plurality of solder balls 322 is bonded along the circumference via reflow. Here, it is preferred that the thickness of the flux range from 0.2 mm to 0.25 mm.

In addition, it is preferred that the sensor chip 320 involve electroless plating, which is performed via a chemical reaction.

The method of fabricating the pulse sensor including the steps of fabricating the sensor chip 320 is described again with reference to FIG. 17. First, the sensor chip 320 is attached to one side of the board 310, in which one or more first holes 312 are formed, so that it closes the first holes 312.

Afterwards, gel 352, which is a pressure transferring member, is disposed in the first holes 312.

Subsequently, a pad 360 is attached to the other side of the board 310 so that the first holes 312 are closed.

Although the method of fabricating the pulse sensor including the dam 340, which is described later, is illustrated in the figure, the method of fabricating the pulse sensor except for the dam 340 can be easily analogized.

Here, it is preferred that the pad 360 have pressing portions 362, which protrude from one and the other surfaces of the portions of the board 310 that correspond to the first holes 312.

In the pulse sensor 71 provided by the foregoing method, a plurality of first holes 312 can be formed in the board 310, spaced apart from each other at regular intervals, and a plurality of sensor chips 320 corresponding to the plurality of first holes 312 can be fixedly attached to the circumference of the first holes 312.

Here, in the step of attaching the sensor chips 320, an epoxy 330 is preferably applied on one surface of the board 310, between the side portions of the sensor chips 320, and between the sensor chips 320 so the sensor chips 320 are fixed to the board 310 and to each other.

In another embodiment, the method of fabricating the pulse sensor 71 of the invention can also includes the step of arranging sticks between the step of attaching the sensor chips 320 and the step of disposing the gel 352, the sticks being arranged lengthwise such that they correspond to the first holes 312.

In the meantime, in a further embodiment, the method of fabricating the pulse sensor 71 also includes the step of attaching a dam 340 between the step of disposing the gel 352 and the step of attaching the pad 360, in which the dam 340 is attached to the board 310 and the pad 360 by arranging the pad 360 between the board 310 and the pad 360 such that the second holes 342 communicate with the first holes 312.

Here, in the step of disposing the gel 352, the gel 352 is disposed in the first and second holes 312 and 342.

Furthermore, the invention can also include the step of arranging the sticks inside the communicating first and second holes 312 and 342, the sticks being arranged lengthwise such that they correspond to the first holes 312 and the second holes 342.

Thanks to the improved structure, the pulse sensor 71 produced by the above-described method of fabricating the pulse sensor 71 exhibits various effects, which have been described in the part of the disclosure in which the structure of the pulse sensor 71 is described.

INDUSTRIAL APPLICABILITY

According to the sphygmomanometer apparatus of the present invention as described above, the arm-fixing device having a concave configuration is provided so that the arm of the person to be examined can be placed in a normal state in the arm-fixing device without being twisted. Consequently, this makes the person to be examined comfortable, thereby making it possible to measure a correct pulse wave from the person.

In addition, according to the sphygmomanometer apparatus of the present invention, even when the person to be examined casually places the arm in the arm-fastening device so that the inner portion of the wrist, the pulse-measuring position, is inclined with respect to the horizontal plane, the pulse sensor can be pressed in the oblique direction in a corresponding way so that it is oriented to be perpendicular to the incline. Consequently, a correct pulse wave can be measured without distortion.

Furthermore, the operator can compare pulse waves of both arms to each other by measuring the pulse waves using one sphygmomanometer apparatus.

In addition, according to the sphygmomanometer apparatus of the present invention, pulse waves can be measured from correct pulse-measuring positions, since it is possible to cope with various curvature characteristics of the surface of the skin of the arm of the person to be examined.

Moreover, the pulse sensor of the present invention has increased durability thanks to the sensor chip being bonded to the board via FDB and the sensor chip has increased sensitivity to the pulse of the person to be examined while decreasing the crosstalk between sensor chips using holes formed in the board and a dam and gel disposed in the holes.

Thanks to the above-described configurations and effects, the present invention has industrial applicability.

The invention claimed is:

1. A pulse sensor comprising:
a board having a first board surface and a second board surface opposite the first board surface and at least one first hole extending through the board from the first board surface to the second board surface;
a sensor chip attached to the first board surface such that the sensor chip closes the first hole of the board and is electrically connected to the board;
a pad attached to the second board surface, wherein the pad-is intended to come into contact with a pulse of a user;
a pressure transferring member disposed inside the first hole of the board such that an input signal, which is received by the pad, is sent to the sensor chip; and
a dam disposed between the board and the pad such that a second hole communicates with the first hole, the dam being attached to the board and the pad, wherein the pressure transferring member is gel disposed in the first hole and the second hole.

2. The pulse sensor of claim 1, wherein the sensor chip includes a plurality of solder balls protruding along a circumference of a surface thereof corresponding to the board, the solder balls being attached to the first board surface, and the gel disposed in the first hole is also disposed between the first board surface and the sensor chip.

3. The pulse sensor of claim 1, wherein the pad comprises a first pad surface and a second pad surface opposite the first pad surface, wherein the first pad surface is in contact with the second board surface and includes pressing portions protruding from the first pad surface and the second pad surface corresponding to the first hole of the board.

4. The pulse sensor of claim 1, wherein a plurality of the first holes is spaced apart from the board at a predetermined interval, a plurality of the sensor chips corresponding to the first holes is fixedly attached to a circumference of the first hole, and an epoxy is applied the first board surface, between side portions of the sensor chips, and between the sensor chips, such that the sensor chips are fixed to the board and to each other.

5. The pulse sensor of claim 1, wherein the pressure transferring member includes a stick buried in the gel, the stick being arranged lengthwise along the first holes and the second holes.

6. A pulse diagnosis apparatus for measuring a pulse of a user, the apparatus comprising:
an arm-fixing recess capable of receiving a portion of an arm of the user, in which a radial bone is located, at an incline such that an inner portion of the arm of the user faces a person the user to be examined;
an arm contact surface provided in a lower portion of the arm-fixing recess, wherein the portion of an the arm, in which the radial bone is located, is supposed to be placed in the arm contact surface;
a body having the arm contact surface in an upper portion thereof;
a main frame provided in a lower end of the body to fix the body;
a horizontal rotation adjustment part spaced apart from a front portion of the body at a first predetermined interval in a first oblique direction, and fixed to the main frame such that the horizontal rotation adjustment part is horizontally rotatable; and
an arm-fixing unit having a vertical rotation adjustment part, wherein the vertical rotation adjustment part is fixedly provided on an upper end of the horizontal rotation adjustment part such that the vertical rotation adjustment part is vertically rotatable;
a horizontal frame distanced a second predetermined interval from a side surface of an the arm-fixing unit, wherein the horizontal frame is elongated and fixed to the main frame in a height direction;
a horizontal control motor fixed to a side surface of the horizontal frame to provide a rotational force for a horizontal movement;
a horizontal ball screw fixedly connected to a rotation shaft of the horizontal control motor such that the horizontal ball screw is rotatable;
a horizontal motion guide fixed to an upper end of the horizontal frame;
a vertical frame in contact with and connected to an upper portion of the horizontal frame, wherein both inner surfaces of a lower portion of the vertical frame are fitted into the horizontal motion guide such that the vertical frame is reciprocally movable;
a horizontal guide block disposed on a lower inner surface of the vertical frame and fitted into the horizontal motion guide;
a horizontal ball screw nut fixed to the lower portion of the vertical frame and meshed with the horizontal ball screw;
a vertical control motor fixed to an upper end of the vertical frame, wherein the vertical control motor provides a rotational force for a vertical movement;

a vertical ball screw fixed to a rotation shaft of the vertical control motor such that the vertical ball screw is rotatable;

a vertical movement guide fixed to a front portion of the vertical frame;

a vertical movement bracket in contact with the front portion of the vertical frame such that the vertical movement bracket is vertically movable;

a vertical guide block provided on both inner portions of a surface of the vertical movement bracket that faces the vertical movement guide, wherein the vertical guide block is capable of being fitted into the vertical movement guide;

a vertical ball screw nut fixed to an inner portion of a side surface of the vertical movement bracket that faces the vertical movement guide, the vertical ball screw nut being meshed with the vertical ball screw;

a first rotation motor fixed to the vertical movement bracket such that the first rotation motor provides an angular rotational force;

a first turntable fixed to a rotation shaft of the first rotation motor such that the first turntable is angularly rotatable;

a first rotation arm fixed to the first turntable such that the first rotation arm is angularly rotatable with respect to the vertical movement bracket;

a second rotation motor fixed to a side surface of the first rotation arm such that the second rotation motor provides an a second angular rotational force;

a second turntable fixed to a rotation shaft of the second rotation motor such that the second turntable is angularly rotatable;

a second rotation arm fixed to the second turntable such that the second rotation arm is angularly rotatable with respect to the first rotation arm;

an actuator fixed to the second rotation arm in a vertical lengthwise direction;

a pulse diagnosis unit fixed to a lower end of the actuator, wherein the pulse diagnosis unit has a pulse sensor for converting a physical value of the pulse into an electrical signal, and is capable of pressing in a second oblique direction, wherein the pulse sensor comprises:

a board having a first board surface and a second board surface opposite the first board surface and at least one first hole extending through the board from the first board surface to the second board surface, a sensor chip attached to the first board surface such that the sensor chip closes the first hole of the board and is electrically connected to the board, a pad attached to the second board surface, wherein the pad is intended to come into contact with the pulse of the user, a pressure transferring member disposed inside the first hole of the board such that an input signal, which is received by the pad, is sent to the sensor chip, and a dam disposed between the board and the pad such that a second hole communicates with the first hole, the dam being attached to the board and the pad, wherein the pressure transferring member is gel disposed in the first hole and the second hole;

a central processing unit fixedly provided in the main frame, wherein the central processing unit processes an electrical signal output from the horizontal control motor, the vertical control motor, the first rotation motor, the second rotation motor, and the actuator;

an image display unit outputting a signal processed by the central processing unit; and an operating unit allowing a processing signal of an operator to be input into the central processing unit.

7. The pulse diagnosis apparatus of claim 6, wherein the horizontal rotation adjustment part of the arm-fixing unit includes a horizontal rotation adjustment recess fixed to the main frame and a horizontal rotation adjustment protrusion fixed to a lower end of the horizontal rotation adjustment part.

8. The pulse diagnosis apparatus of claim 6, wherein the vertical rotation adjustment part of the arm-fixing unit includes a vertical rotation adjustment recess fixed to an upper end of the horizontal rotation adjustment part and a vertical rotation adjustment protrusion fixed to a lower end of the vertical rotation adjustment part.

9. The pulse diagnosis apparatus of claim 6, wherein a portion of the arm contact surface, which is intended to come into contact with a wrist of the arm of the person to be examined, is formed to be higher than a portion of the arm contact surface, which is intended to come into contact with an ankle of the arm of the person to be examined, at a predetermined height.

10. The pulse diagnosis apparatus of claim 6, wherein the arm-fixing unit includes parts that are provided on both sides of the pulse diagnosis unit and are distanced a predetermined interval from each other.

11. The pulse diagnosis apparatus of claim 6, wherein the first rotation arm has a length ranging from 150 mm to 250 mm.

12. The pulse diagnosis apparatus of claim 6, wherein a distance in an oblique direction between the pulse diagnosis unit and the arm-fixing unit ranges from 200 mm to 300 mm, the arm-fixing unit being distanced a predetermined interval from a side surface of the pulse diagnosis unit.

13. The pulse diagnosis apparatus of claim 11, wherein a distance in an oblique direction between the pulse diagnosis unit and the arm-fixing unit ranges from 200 mm to 300 mm, the arm-fixing unit being distanced a predetermined interval from a side surface of the pulse diagnosis unit.

14. The pulse diagnosis apparatus of claim 6, wherein the second rotation arm of the pulse diagnosis unit-further includes a laser pointing unit for pointing to a pulse-measuring position of a wrist of a person to be examined.

15. The pulse diagnosis apparatus of claim 11, wherein the second rotation arm of the pulse diagnosis unit further includes a laser pointing unit for pointing to a pulse-measuring position of a wrist of a person to be examined.

16. The pulse diagnosis apparatus of claim 12, wherein the second rotation arm of the pulse diagnosis unit further includes a laser pointing unit for pointing to a pulse-measuring position of a wrist of a person to be examined.

* * * * *